United States Patent
Freitas Schwan et al.

(10) Patent No.: US 11,767,502 B2
(45) Date of Patent: Sep. 26, 2023

(54) STABILITY OF SILAGE INOCULANTS AND METHODS FOR IMPROVING AEROBIC STABILITY OF SILAGE

(71) Applicants: DANSTAR FERMENT AG, Zug (CH); FEDERAL UNIVERSITY OF LAVRAS, Lavras MG (BR)

(72) Inventors: Rosane Freitas Schwan, Lavras (BR); Carla Luiza Silva Avila, Lavras (BR); Jose Cardoso Pinto, Lavras (BR); Eric Chevaux, Blagnac (FR); Renato Schmidt, Milwaukee, WI (US)

(73) Assignees: DANSTAR FERMENT AG, Zug (CH); FEDERAL UNIVERSITY OF LAVRAS, Lavras (BR)

( * ) Notice: Subject to any disclaimer, the term of this patent is extended or adjusted under 35 U.S.C. 154(b) by 78 days.

(21) Appl. No.: 17/249,024

(22) Filed: Feb. 17, 2021

(65) Prior Publication Data
US 2021/0198758 A1 Jul. 1, 2021

Related U.S. Application Data

(63) Continuation of application No. 14/906,132, filed on Jan. 19, 2016, now abandoned.

(30) Foreign Application Priority Data

Jul. 18, 2013 (EP) ..................................... 13177054

(51) Int. Cl.
| | | |
|---|---|---|
| A23K 40/00 | (2016.01) | |
| C12N 1/20 | (2006.01) | |
| A23K 50/10 | (2016.01) | |
| A23K 50/75 | (2016.01) | |
| A23K 50/30 | (2016.01) | |
| A23K 30/18 | (2016.01) | |
| C12R 1/225 | (2006.01) | |

(52) U.S. Cl.
CPC .............. *C12N 1/205* (2021.05); *A23K 30/18* (2016.05); *A23K 40/00* (2016.05); *A23K 50/10* (2016.05); *A23K 50/30* (2016.05); *A23K 50/75* (2016.05); *C12N 1/20* (2013.01); *C12R 2001/225* (2021.05)

(58) Field of Classification Search
CPC ............ C12N 1/205; C12N 1/20; C12R 1/225
USPC ........................................................ 426/61
See application file for complete search history.

(56) References Cited

U.S. PATENT DOCUMENTS

| | | | |
|---|---|---|---|
| 6,326,037 B1 | 12/2001 | Mann et al. | |
| 6,337,068 B1 * | 1/2002 | Hendrick | C12N 1/205 |
| | | | 435/252.1 |
| 2003/0175307 A1 | 9/2003 | Garner et al. | |
| 2008/0095890 A1 | 4/2008 | Watson | |
| 2009/0028993 A1 * | 1/2009 | Chan | A23K 30/00 |
| | | | 426/2 |
| 2009/0081330 A1 * | 3/2009 | Kung, Jr. | A23K 10/37 |
| | | | 426/54 |
| 2010/0080783 A1 | 4/2010 | Watson | |

FOREIGN PATENT DOCUMENTS

| | | |
|---|---|---|
| EP | 0 311 469 A2 | 4/1989 |
| JP | H02-501266 A | 5/1990 |
| RU | 2243999 C2 | 1/2005 |
| WO | 89/01970 A2 | 3/1989 |
| WO | 00/00040 A1 | 1/2000 |

OTHER PUBLICATIONS

Josson, K. et al. Plasmids. 21:9-20 (Year: 1989).*
Zakaria, et al. Anim. Nut. and Feed Technol. 12:55-62 (Year: 2012).*
Office Action for Chilean Patent Application No. 201600123 dated Jan. 15, 2016 with English translation provided.
Office Action for Chinese Patent Application No. 201480044449.6 dated Mar. 25, 2019 with English translation provided.
Office Action for European Patent Application No. 14 752 947.3 dated Jul. 27, 2017.
Office Action for Japanese Patent Application No. 2016-526729 dated May 15, 2018 with English translation provided.
Hielrich, Kenneth, ed., "Official Methods of Analysis of the Association of Official Analytical Chemists," Fifteenth Edition, 1990.
Avila et al., "Effects of an indigenous and a commercial Lactobacillus buchneri strain on quality sugar cane silage," The Journal of British Grassland Society, 64, 384-394, 2009.
Dubois et al., "Colorimetric Method for Determination of Sugars and Related Substances," Analytical Chemistry, vol. 28, 1956, 350-356.
Holden, "Comparison of methods of in vitro dry matter digestibility for ten 565 feeds," Journal of Dairy Science, vol. 82, 1999, 1791-1794.
Zakaria et al., "Effect of Bacteria Inoculants on Corn Silage Quality," Animal Nutrition and Feed Technology (2012) 12: 556-62.

(Continued)

*Primary Examiner* — Hamid R Badr
(74) *Attorney, Agent, or Firm* — NIXON & VANDERHYE

(57) ABSTRACT

There is provided a method for treating silage which includes adding to the silage a silage inoculant including a silage preserving effective amount of *Lactobacillus hilgardii*. The silage inoculant being effective to prevent or reduce aerobic spoilage.

14 Claims, No Drawings

(56) References Cited

OTHER PUBLICATIONS

Office Action for Russian Patent Application No. 2016105235/13(008430) dated Mar. 13, 2018 with English translation provided.
International Search Report, dated Oct. 8, 2014, from corresponding International Application No. PCT/IB2014/062814.
Josson K et al: "Characterization of a gram-positive broad-host-range plasmid isolated from Lactobacillus hilgardii", Plasmid, New York,NY, US, vol. 21, No. 1, Jan. 1, 1989 (Jan. 1, 1989), pp. 9-20, XP024799449, ISSN: 0147-619X, DOI: 10.1016/0147-619X(89)90082-6 [retrieved on Jan. 1, 1989].
Stefan Heinl et al: "Insights into the completely annotated genome of Lactobacillus buchneri CD034, a strain isolated from stable grass silage", Journal of Biotechnology, vol. 161, No. 2, Oct. 1, 2012 (Oct. 1, 2012), pp. 153-166, XP055081357, ISSN: 0168-1656, DOI: 10.1016/j.jbiotec.2012.03.007.

* cited by examiner

STABILITY OF SILAGE INOCULANTS AND METHODS FOR IMPROVING AEROBIC STABILITY OF SILAGE

STATEMENT OF RELATED CASES

This application is a continuation of Ser. No. 14/906,132 filed Jan. 10, 2016, which is the U.S. national stage of PCT/IB2014/062814 filed Jul. 3, 2014, which claims the benefit of EP 13177054.7 filed Jul. 18, 2013, all of the preceding applications being herein expressly incorporated by reference.

BACKGROUND OF THE INVENTION

The present description relates to silage. More specifically to silage inoculants and method of use of silage inoculants for enhancing aerobic stability of silage.

Silage is fermented, high-moisture forage to be fed to ruminants, such as cud-chewing animals like cattle and sheep. The silage is fermented and stored in a storage silo, a process called ensilage. Silage is most often made from grass or cereal crops, including ryegrass, alfalfa, fescue, corn (maize) or sorghum. Silage is made from the entire plant, or part of it. Silage can also be made from many other field crops, including sugar cane, and other names such as, for example oatlage for oats, haylage for alfalfa are sometimes used when this is done. Sometimes a mixture is used, such as oats and peas.

The production of silage and the associated crop husbandry have over recent years developed to an extent that a number of different processes can be defined. These are: (i) the ensiling of young grass with particularly low dry matter, e.g. less than 25%; (ii) the ensiling of higher dry matter, more mature grasses, or the ensiling of high dry matter but young grass achieved by wilting; and (iii) the ensiling of whole maize including stover and cob, usually at a dry matter concentration of about 35%, and whole crop cereals, e.g. wheat, at 45-50% dry matter.

While these processes generally produce a good yield, they are not without their problems. Particularly in cases (ii) and (iii), one major problem occurs on a regular basis. This is the phenomenon known as aerobic spoilage. The process of aerobic spoilage occurs at opening of the silo, when the material is exposed to air. It can be divided into specific phases. First, there is an initial phase in which yeasts and sometimes acetic acid bacteria start to respire the preserving organic acids, raising the silage pH, and the temperature begins to rise. After an initial rise in pH, there is a secondary phase in which the activity of bacilli is apparent, and is associated with increasing temperature. A further phase includes activity of various microorganisms including fungi.

In those silages which contain a substantial content of dry matter, i.e. over 30%, the problem of spoilage is particularly acute. Spoilage is seen to a greater or lesser extent once a silage clamp is opened and exposed to air.

Biological additives such as bacterial inoculants have been used widely to improve the silage process, primarily to increase the extent and rate of lactic acid production, and guard against aerobic spoilage. U.S. Pat. No. 6,326,037 to Mann et al. provides methods and compositions for improving this situation. In particular, there described is based at least in part on identifying the aerobic spoilage process as being closely related to heating in the clamp on exposure to the ingress of air. Subsequent examination of such silages showed high concentration of thermophilic Gram-positive bacteria, including bacilli, yeasts and molds. This apparently demonstrates the onset of a secondary fermentation, akin to that of composting (the primary fermentation being the ensiling process). In this fermentation stage, yeast and moulds predominate. It appears that, in order to prevent spoilage, the three main categories of organisms that need to be killed or suppressed are spore-forming bacteria, yeasts and fungi. To eliminate only one category may lead to the proliferation of the remaining categories, so that spoilage is not prevented.

Accordingly, Mann teaches spoilage prevention by using treatment organisms that, at least in the first instance, inhibit microorganisms that initiate aerobic spoilage, notably yeasts and, at the surface of silage, fungi. An organism capable of doing this may also inhibit the development of other spoilage microorganisms, and may be identified by screening. An organism of the species *Lactobacillus buchneri*, which meets this requirement, has been deposited at the National Collection of Industrial and Marine Bacteria on 13 Feb. 1996. Its accession number is 40788.

While treatments using *Lactobacillus buchneri* reduce spoilage in silage, they do so to only a limited extent. Accordingly, the remains a need for an improved silage treatment, particularly for improving aerobic stability of silage while increasing the amount of dry matter recovered.

SUMMARY OF THE DISCLOSURE

In an aspect, there is provided a method for treating silage. The method comprises adding to the silage a silage inoculant comprising a silage preserving effective amount of *Lactobacillus hilgardii*.

The silage inoculant is effective to prevent or reduce aerobic spoilage.

In another aspect, there is provided a silage inoculant comprising a silage preserving effective amount of *Lactobacillus hilgardii*.

In an aspect of the silage inoculant, the silage inoculant further comprises a carrier.

In a further aspect, there is provided a silage comprising a silage preserving effective amount of *Lactobacillus hilgardii*.

In an aspect of the method, in the silage inoculant and the silage, the *Lactobacillus hilgardii* is at least one of *Lactobacillus hilgardii*, strain SIL51, having accession number CNCM I-4784 filed on Jun. 26, 2013 and *Lactobacillus hilgardii*, strain SIL52, having accession number CNCM I-4785 filed on Jun. 26, 2013, or genetic equivalents thereof. Said strains have been deposited by Lallemand SAS 19 rue des Briquettiers, 31702 Blagnac Cedex, France.

In an aspect of the method, the silage inoculant further comprises a carrier.

In a yet further aspect, there is provided an isolated strain of *Lactobacillus hilgardii*, strain SIL 51, having accession number CNCM I-4784 filed on Jun. 26, 2013 or genetic equivalents thereof.

In another aspect, there is provided an isolated strain of *Lactobacillus hilgardii*, strain SIL 52, having accession number CNCM I-4785 filed on Jun. 26, 2013 or genetic equivalents thereof.

DETAILED DESCRIPTION

According to the present description, lactic acid bacteria have been isolated and purified which improve the aerobic stability of ensiled forage. More specifically, *Lactobacillus hilgardii* have been shown to enhance aerobic stability of silage. Furthermore, when inoculated on silage, the *Lacto-* bacillus hilgardii strains produce silage that is well preserved and in which the onset of secondary fermentation associated with aerobic spoilage and heating is reduced or prevented.

The stains of the present description were isolated from sugarcane (*Saccharum* spp.) silage. After purification and isolation of the strains, taxonomic studies were done to identify the strains. Two of them were identified as *Lactobacillus hilgardii* and given the prototype number SIL51 and SIL52.

Therefore, the present description provides silage inoculants and method of use of silage inoculants for enhancing aerobic stability of silage.

The term "silage preserving effective amount" when used herein will be understood to refer to an amount which is at least sufficient to preserve the silage. Thus the amount is at least sufficient to improve the stability of silage, but preferably is an amount sufficient to improve the stability of silage while increasing the amount of dry matter recovered.

The term "aerobic stability" when used herein will be understood to refer to the number of hours that the temperature of the silage remained stable before rising more than 2° C. above the ambient temperature.

Reference will now be made to the embodiments described herein. It is understood that no limitation of the scope of the disclosure is thereby intended. It is further understood that the present disclosure includes any alterations and modifications to the illustrated embodiments and includes further applications of the principles of the disclosure as would normally occur to one skilled in the art to which this disclosure pertains.

In an embodiment, there is provided a method for treating silage. The method comprises the step of adding to the silage a silage inoculant comprising a silage preserving effective amount of *Lactobacillus hilgardii*. The silage inoculant being effective to prevent or reduce aerobic spoilage.

There is also provided a silage inoculant comprises at least a strain of *Lactobacillus hilgardii*. More specifically, the silage inoculant comprises a silage preserving effective amount of the species *Lactobacillus hilgardii*.

In an embodiment of the method and the silage inoculants described above, the strain of *Lactobacillus hilgardii* may be an isolated strain of *Lactobacillus hilgardii* CNCM I-4784 filed on Jun. 26, 2013 (SIL51), CNCM I-4785 filed on Jun. 26, 2013 (SIL52), or genetic equivalents thereof. It is understood that mutants or genetic equivalents of strains CNCM I-4784 filed on Jun. 26, 2013 (SIL51) and CNCM I-4785 filed on Jun. 26, 2013 (SIL52) which retain the functional activity of improving aerobic stability of forage as described in the present description are also contemplated.

Regardless of the manner in which mutations or the genetic equivalents are induced, the critical issue is that they function to improving aerobic stability of silage as described for the parent species and/or strain. In other words, the present description includes mutations resulting in such minor changes as, for example, minor taxonomical alterations.

The silage inoculants according to the present description may be in either liquid of solid form and may comprises additional bacterial strains. The silage inoculants according to the present description may comprise a suitable carrier or may be used as is. In solid form, the silage incoculant may comprise solid carrier. The suitable carrier may be in aqueous or non-aqueous liquid form or in solid form. Examples of aqueous or non-aqueous liquid form carrier include water, oils and paraffins. Examples of solid form carrier include organic or inorganic carrier such as, for example, maltodextrin, starches, calcium carbonate, cellulose, whey, ground corn cobs, and silicone dioxide. The solid composition can be applied directly to the forage in the form of a light powder dusting, or if it is disbursed in a liquid carrier it can successfully be sprayed on the forage. It is understood that any other suitable carrier for the purpose of the present description may be used.

It appears that the inhibitory substance may be a secondary metabolite. Therefore, its full effect may not be seen if, when used in silage, that silage is opened too soon. The silage is preferably kept closed for at least 30 days, and more preferably for at least 45 days. The optimum periods may depend inter alia on the size of the silage mass, and the nature of the ensiled material.

Materials that are suitable for ensiling in accordance with the present description are those susceptible to aerobic spoilage. The materials usually contain at least 20% by weight of dry matter. Such materials include, for example, rye or traditional grass, maize, including high moisture corn, whole plant corn, Lucerne, wilted grass, wheat, legumes, sorghum, sunflower, barley, other whole crop cereal and other field crop such as sugarcane. The silage may be in bales (a form particularly susceptible to aerobic spoilage), oxygen limiting bags, bunkers, upright stave silos, oxygen limiting silos, bags, piles or any other suitable form of storage which may be susceptible to aerobic spoilage. In an embodiment, the silage inoculant of the present description may be used with any suitable animal feed, whether solid or liquid, for the purpose of feeding animals such as, for example, pigs, poultry or ruminants.

The following examples serve to further describe and define the invention, and are not intended to limit the invention in any way.

EXAMPLES

Example 1

Silage was made with fresh cut sugar cane from plants that were approximately 12 months old. The sugar cane was manually harvested and chopped using a laboratory-type chopper (Pinheiro, model: PP-47) to an approximate length of 30 mm. 3 kg of the chopped material was mixed with the inoculants and conditioned in PVC plastic buckets (mini-silos, 10 cm in diameter and 60 cm in length), which were sealed with tight lids containing Bunsen valves for gas release. The material in the silo was compacted to a density of approximately 630±19.9 kg m-3. The mini-silos were stored at room temperature and analyzed after 61 days of storage, and three replicates were prepared for each silo.

Silage was produced using the *Lactobacillus plantarum* SIL 34 (*L. plantarum* are commonly used as silage inoculant) and the *Lactobacillus hilgardii* strains SIL 51 (CNCM I-4784 filed on Jun. 26, 2013) and SIL 52 (CNCM I-4785 filed on Jun. 26, 2013) as inoculants. The *Lactobacillus plantarum* and the *Lactobacillus hilgardii* strains were isolated from sugarcane silage and identified with 98% sequence identity. Silage without any inoculants was used as a control. The inoculants were cultured according to Avila et al. (Effects of an indigenous and a commercial *Lactobacillus buchneri* strain on quality of sugar cane silage, Grass Forage Sci 6:384-394, 2009). After the final culture, the number of cells was counted on De Man Rogosa Sharpe agar (Oxoid CM361, Basingstoke, Hampshire, England), and the concentration of the culture was adjusted to 9 log cfu ml-1. The culture was mixed with 80 mL of sterile distilled water and sprayed onto the chopped sugar cane to a final concentration of 6 log cfu g-1 herbage. The control received the same amount of water without any bacteria. For each treatment, a separate sprayer was used to avoid cross-contamination.

The weights of the empty and full silos were recorded. After sealing, the silos were maintained at room temperature (average of 25° C.) and protected from sunlight and rain. After 61 days of ensiling, the full silos were weighed prior to opening. The loss of dry matter (DM) was calculated using the weight and DM content of the fresh forage and silage.

Inoculation with the *Lactobacillus plantarum* (SIL 34) resulted in silage with a lower DM content, a higher DM losses and a higher NDF compared to the other strains and the control. In the silage inoculated with *Lactobacillus hilgardii* strains SIL 51 and SIL 52, lower DM losses were found compared to the SIL 34 and the control (Table 1). Inoculation with these same strains also resulted in silage with a higher DM content and lower NDF. The inoculants did not influence the pH value and soluble carbohydrate content of the silage.

TABLE 1

Chemical composition of sugarcane silages at day 61 of ensiling without inoculants and with different inoculants

| Silage treatments | $DM^b$ (g kg$^{-1}$ $FM^c$) | Losses DM (%) | $NDFd$ $WSCe$ (g kg − 1 DM) | pH | $LABf$ Yeasts Log cfu. g − 1 |
|---|---|---|---|---|---|
| control | 246.2b | 22.61a | 617.9b 25.3 | 3.60 | 8.16a 5.38b |
| SIL 34 | 241.3b | 26.49a | 676.9a 24.6 | 3.64 | 6.93b 5.08a |
| SIL 51 CNCM I-4784 filed on Jun. 26, 2013 | 264.8a | 14.90b | 598.0b 23.4 | 3.61 | 8.36a 4.61b |
| SIL 52p CNCM I-4785 filed on Jun. 26, 2013 | 259.6a | 15.39b | 616.7b 21.1 | 3.66 | 8.40a 4.83b | b-Dry matter content; c-Fresh matter; d-neutral detergent fibre; e-water-soluble carbohydrates; f: lactic acid bacteria.

Mean values with different letters in a column are significantly different ($p<0.05$)

Analytical Procedures

On the opening day, two samples were removed from each mini-silo, and all of the contents of the mini-silo were homogenized. One of the samples was weighed and dried in a fan-assisted oven at 55° C. for 96 h; another sample was used to make a water extract to determine the pH value, evaluate the microbial population and detect fermentation end products.

The dried samples were ground in a Willey-type grinder using a 30-mesh sieve and stored in labeled plastic pots. The samples were analyzed for DM content (AOAC (1990) Official methods of analyses. 15th edition. Washington, D.C., USA: Association of Official Analytical Chemists), water-soluble carbohydrates (WSC) by the phenol method (Dubois M, Gilles K A, Hamilton J K, Rebers P A, Smith F (1956) Colorimetric method for determination of sugars and related substances. Anal Chem 28:350-356.) and neutral detergent fibre (NDF) as described by Holden (Comparison of methods of in vitro dry matter digestibility for ten 565 feeds. J Dairy Sci 82:1791-1794; 1999), using an Ankom Fiber Analyser (ANKOM Technology Corporation, Fairport, N.Y., USA) and expressed on a DM basis.

The levels of ethanol, 1,2-propanediol and lactic, acetic, propionic and butyric acids were measured by HPLC according to Carvalho et al. (Effects of propionic acid and *Lactobacillus buchneri* (SIL72) addition on fermentative and microbiological characteristics of sugar cane silage treated with or without calcium oxide. Grass Forage Sci doi: 10.1111/j.1365-2494.2012.00863.x). The acids, ethanol and 1,2-propanediol were identified by comparing their retention times with the retention times of known standards. The concentrations of the identified compounds were determined by the external calibration method. The HPLC apparatus (Shimadzu model LC-10Ai; Shimadzu Corp., Tokyo, Japan) was equipped with a dual detection system consisting of an ultraviolet detector (UV-VisSPD-10Ai) and a refractive index detector (RID 10A). An ion exclusion column from Shimadzu (Shim-pack SCR-101H; 7.9 mm×30 cm) operated at 50° C. was used for the chromatographic separation. The mobile phase consisted of a 100 mM perchloric acid solution with a flow rate of 0.6 mL min-1. The acids were detected by UV absorbance (210 nm). Ethanol and 1,2-propanediol were identified using the refractive index detector. The pH values were measured with a potentiometer (Expandomatic Beckman SS-2).

As shown in Table 2, the silage inoculated with the SIL 51 and SIL 52 strains with the lowest loss of DM had a lower concentration of ethanol than the SIL 34 and the control. The SIL 34 strain that resulted in the silage with the greatest loss of DM produced the highest amount of lactic acid. In the silages inoculated with SIL 51 and SIL 52 strains, higher concentrations of acetic acid and 1,2-pronanediol were also noted compared to the SIL 34 and the control. The propionic acid levels were similarly low, consistent with the SIL 34 and the control silage.

TABLE 2

Lactic, acetic, propionic and butyric acids and ethanol and 1,2-propanodiol of sugarcane silages at day 61 of ensiling without inoculants and with *Lactobacillus hilgardii* inculants

| Silage tretaments | Lactic Acid (g kg-l DM) | Acetic Acid (g kg-l DM) | Propionic Acid (g kg-1 DM) | Butyric Acid (g kg-1 DM) | Ethanol (g kg-1 DM) | 1,2-propanodiol (g kg-1 DM) |
|---|---|---|---|---|---|---|
| control | 46.6a | 9.7b | 3.1b | 0.0b | 137.0a | 1.7b |
| SIL 34 | 43.7a | 3.3c | 6.4a | 3.5a | 185.8a | 0.6c |
| SIL 51 CNCM I-4784 filed on Jun. 26, 2013 | 34.6b | 19.7a | 4.0b | 1.2b | 39.9c | $3.27^a$ |
| SIL 52 CNCM 1-4785 filed on Jun. 26, 2013 | 31.4b | 22.5a | 4.1b | 1.3b | 44.4c | $3.98^a$ |

Microbiological Analysis

Samples (70 g) of fresh forage and sugar cane silage after 61 d of incubation were mixed with 630 mL of 0.1% sterile peptone water and stirred in an orbital mixer with 120 rpm for 20 min. Subsequently, 10-fold dilutions were prepared to quantify the different microbial groups. Lactic acid bacteria (LAB) were enumerated using MRS agar (De Man Rogosa Sharpe, Difco, Detroit, Mich., USA) containing 0.1% cysteine HCl (Merck, Dasmstadt, Germany) and 0.4% cycloheximide (0.4%) (Sigma) after anaerobic incubation (AnaeroGen; Oxoid, Basingstoke, UK). The plates were incubated at 30° C. for 48 h. Yeast and filamentous fungi were enumerated on Dichloran Rose Bengal Chloramphenicol Medium (DRBC, Difco; Becton Dickinson, Sparks, Md., USA) after incubating the plates at 28° C. for 72 h. For all of the microorganisms, only plates containing between 30 and 300 cfus were enumerated.

Assessment of Aerobic Stability of Silages

After 90 d of ensiling, the mini-silos were opened, and triplicate samples of approximately 3 kg were removed from each mini-silo and placed in 5-kg plastic buckets to assess their aerobic stability. A thermometer was inserted into the silage mass to a depth of 10 cm for 7 d. The containers were kept in a room with a controlled temperature of 26° C. (±1.5° C.). The silage temperature was recorded every 8 h. The ambient temperature was measured using a thermometer located close to the buckets. Aerobic stability was defined as the number of hours that the silage remained stable before rising more than 2° C. above the ambient temperature.

TABLE 3

Aerobic stability of sugarcane silages with inoculants

| Silage treatments | Aerobic stability (hours) | Maximum temperature (° C.) | Time for maximum Temperature(hours) |
|---|---|---|---|
| control | 21.3 ± 14.6 | 43.7 ± 0.6 | 45.3 ± 12.2 |
| SIL 34 | 24.0 ± 0.0 | 43.7 ± 1.4 | 37.3 ± 9.2 |
| SIL 51 CNCM I-4784 filed on Jun. 26, 2013 | 26.7 ± 4.6 | 44.0 ± 1.0 | 50.7 ± 9.2 |
| SIL 52 CNCM I-4785 filed on Jun. 26, 2013 | 21.3 ± 4.6 | 44.3 ± 1.5 | 48.0 ± 16 |

As shown in table 3, the temperature of the control silage was stable for approximately 21.3 h, while that of the silage inoculated with the SIL 51SIL and 52 strains lost temperature stability after 26.7 and 21.3 h respectively, after the opening of the silo. The time to reach maximum temperature was longer for both SIL 51 and 52 strains. Therefore, SIL 51 and SIL 52 strains resulted in silage with superior temperature stability to the SIL 34 and the control silage.

The silage inoculated with the *Lactobacillus plantarum* strain SIL 34 that produced lactic acid lost temperature stability after 24 h. However, the SIL 34 strain resulted in silage with a higher content of ethanol, higher yeast counts and greater DM losses. The SIL 51 and SIL 52 strains provided better characteristics to silage, such as a smaller yeast population, lower ethanol content and less DM losses.

Example 2: Aerobic Stability of Corn Silages

Corn silage was produced in micro-silos as described in Example 1 using the *Lactobacillus buchneri*, NCIMB 40788 (U.S. Pat. No. 6,326,037 to Mann et al.), the *Lactobacillus plantarum* SIL 34 and the *Lactobacillus hilgardii* strains SIL 51 (CNCM I-4784 filed on Jun. 26, 2013) and SIL52 (CNCM I-4785 filed on Jun. 26, 2013) as inoculants. Silage without any inoculants was used as a control. The inoculants were cultured as described in Example 1.

After 90 d of ensiling, the mini-silos were opened, and samples of approximately 3 kg were removed from each mini-silo and placed in 5 kg plastic buckets to assess the aerobic stability. A data logger was inserted into the silage mass, at a depth of 10 cm, for 7 days. The ambient temperature was measured using a data logger located close to the buckets. The data on aerobic stability of silages are shown in Table 4.

TABLE 4

Aerobic stability of corn silages with inoculants.

| Treatment | Dose | Maximum temperature (° C.) average | | Time to reach maximum temperature (h) average | | Aerobic stability (h) average | |
|---|---|---|---|---|---|---|---|
| Control | cfu/g | 34.2 | 34.2 | 72.3 | 72.3 | 42.7 | 42.7 |
| STL 34 | 1 | 38.0 | 38 | 37.2 | 37.4 | 21.8 | 17.4 |
|  | 2 | 38.8 |  | 37.7 |  | 13.0 |  |
| SIL 51 CNCM I-4784 filed on Jun. 26, 2013 | 1 | 31.0 | 30.9 | 133.1 | 138.3 | 73.8 | 73.05 |
|  | 2 | 30.8 |  | 143.5 |  | 72.3 |  |
| SIL 52 CNCM I-4785 filed on Jun. 26, 2013 | 1 | 30.8 | 32.05 | 132.2 | 112.3 | 49.0 | 53.35 |
|  | 2 | 33.3 |  | 92.5 |  | 57.7 |  |
| NCIMB 40788 | 1 | 33.7 | 33.1 | 85.5 | 101.1 | 42.8 | 60.5 |
|  | 2 | 32.5 |  | 116.7 |  | 77.7 |  |

Dose 1 = $10^5$ cfu/g; 2 = $10^6$ cfu/g

As shown in table 4, the temperature of the control silage was stable for approximately 42.7 h, while that of the silage inoculated with the SIL 51 and 52 strains lost temperature stability after 73.05 and 53.35 h respectively, after the opening of the silo. The silage inoculated with SIL 34 was stable for 17.4 hours. The silage inoculated with the *Lactobacillus buchneri* NCIMB 40788 was stable for 60.5 h. The SIL 51 and SIL 52 strains resulted in silage with superior temperature stability to the silage inoculated with SIL 34 and the control silage. The SIL 51 and SIL 52 strains also resulted in silage with superior temperature stability to the NCIMB 40788 silage.

While the invention has been described in connection with specific embodiments thereof, it will be understood that it is capable of further modifications and this description is intended to cover any variations, uses, or adaptations of the invention following, in general, the principles of the invention and including such departures from the present disclosure that come within known or customary practice within the art to which the invention pertains and as may be applied to the essential features hereinbefore set forth, and as follows in the scope of the appended claims.

The invention claimed is:

1. A silage inoculant comprising a silage preserving effective amount of *Lactobacillus hilgardii*, wherein said silage preserving effective amount improves aerobic stability of silage while increasing the amount of dry matter recovered, and wherein aerobic stability refers to the number of hours that the temperature of the silage remained stable before rising more than 2° C. above the ambient temperature.

2. The silage inoculant according to claim 1, wherein the *Lactobacillus hilgardii* is at least one of *Lactobacillus hilgardii*, strain SIL51, having accession number CNCM I-4784 filed on Jun. 26, 2013 and *Lactobacillus hilgardii*, strain SIL52, having accession number CNCM I-4785 filed on Jun. 26, 2013.

3. A method for treating silage, comprising adding to the silage a silage inoculant comprising a silage preserving effective amount of *Lactobacillus hilgardii*, wherein said silage preserving effective amount improves aerobic stability of silage while increasing the amount of dry matter recovered, and wherein aerobic stability refers to the number of hours that the temperature of the silage remained stable before rising more than 2° C. above the ambient temperature.

4. The method according to claim 3, wherein the *Lactobacillus hilgardii* is at least one of *Lactobacillus hilgardii*, strain SIL51, having accession number CNCM I-4784 filed on Jun. 26, 2013 and *Lactobacillus hilgardii*; strain SIL52, having accession number CNCM I-4785 filed on Jun. 26, 2013.

5. The method according to claim 3, wherein the silage is traditional grass, maize, Lucerne, wilted grass, crop cereal or sugarcane silage.

6. The method according to claim 3, wherein the silage is in a bale, a bag, a bunker, a stave silo or a silo.

7. A silage comprising a silage preserving effective amount of *Lactobacillus hilgardii*, wherein said silage preserving effective amount improves aerobic stability of silage while increasing the amount of dry matter recovered, and wherein aerobic stability refers to the number of hours that the temperature of the silage remained stable before rising more than 2° C. above the ambient temperature.

8. The silage of claim 7, wherein the *Lactobacillus hilgardii* is at least one of *Lactobacillus hilgardii*; strain SIL51, having accession number CNCM I-4784 filed on Jun. 26, 2013 and *Lactobacillus hilgardii*; strain SIL52, having accession number CNCM I-4785 filed on Jun. 26, 2013.

9. The silage inoculant of claim 1 comprising an isolated strain of *Lactobacillus hilgardii*, strain SIL51, having accession number CNCM I-4784 filed on Jun. 26, 2013.

10. The silage inoculant of claim 1 comprising an isolated strain of *Lactobacillus hilgardii*, strain SIL52, having accession number CNCM I-4785 filed on Jun. 26, 2013.

11. The method according to claim 4, wherein the silage is traditional grass, maize, Lucerne, wilted grass, crop cereal or sugarcane silage.

12. The method according to claim 4, wherein the silage is in a bale, a bag, a bunker, a stave silo or a silo.

13. The method according to claim 5, wherein the silage is in a bale, a bag, a bunker, a stave silo or a silo.

14. The method according to claim 11, wherein the silage is in a bale, a bag, a bunker, a stave silo or a silo.

* * * * *